US00PP20046P3

(12) United States Plant Patent
Zary

(10) Patent No.: US PP20,046 P3
(45) Date of Patent: Jun. 2, 2009

(54) SHRUB ROSE PLANT NAME 'JACPLUCO'

(50) Latin Name: *Rosa hybrida*
Varietal Denomination: JACpluco

(75) Inventor: Keith W. Zary, Thousand Oaks, CA (US)

(73) Assignee: Jackson & Perkins Wholesale, Inc., Hodges, SC (US)

( * ) Notice: Subject to any disclaimer, the term of this patent is extended or adjusted under 35 U.S.C. 154(b) by 132 days.

(21) Appl. No.: 11/824,538

(22) Filed: Jun. 29, 2007

(65) Prior Publication Data

US 2009/0031459 P1 Jan. 29, 2009

(51) Int. Cl.
*A01H 5/00* (2006.01)

(52) U.S. Cl. ..... Plt./102

(58) Field of Classification Search ..... Plt./102
See application file for complete search history.

*Primary Examiner*—Kent L Bell
(74) *Attorney, Agent, or Firm*—Klarquist Sparkman, LLP

(57) ABSTRACT

Shrub rose plant having flowers with dark purple flower color; strong lemon fragrance; vigorous, upright growth; large clusters, ease of rooting as a softwood or hardwood cutting; and excellent resistance to rust and powdery mildew.

1 Drawing Sheet

Genus and species: *Rosa hybrida.*
Variety denomination: 'JACpluco'.

ORIGIN OF THE INVENTION

The present invention relates to a new and distinct variety of a shrub rose plant named 'JACpluco' which was originated by me by crossing an unnamed seedling (female parent, unpatented), the parentage of the unnamed seedling is unnamed seedling (unpatented)×unnamed seedling (unpatented), with the variety 'JACshok' (male parent, P.P. 11562).

BACKGROUND OF THE INVENTION

The primary objective of this breeding was to produce a new shrub rose variety having the deep purple flower color and upright growth of the female parent combined with the fragrance of the male parent.

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which I am aware:

1. Dark purple flower color.
2. Strong lemon fragrance.
3. Vigorous, upright growth.
4. Large clusters.
5. Ease of rooting as a softwood or hardwood cutting.
6. Excellent resistance to rust and powdery mildew.

Asexual reproduction of this new variety by cuttings, as performed at Wasco, Calif., shows that the foregoing characteristics and distinctions come true to form and are established and transmitted through succeeding propagations.

COMPARISON WITH PARENTS

The female parent differs in petal count (5 for the female parent versus 10–15 for 'JACpluco'). The male parent differs in flower color (light lavender for the male parent versus dark purple for 'JACpluco').

COMPARISON WITH SIMILAR VARIETY

The most similar variety is believed to be 'JACpursh' (PP 11251). 'JACpluco' differs from 'JACpursh' in scent (lemon for 'JACpluco' versus spicy for 'JACpursh') and in petal count (10–15 for 'JACpluco' versus 15–20 'JACpursh').

BRIEF DESCRIPTION OF THE ILLUSTRATION

The accompanying illustration shows typical specimens of the vegetative growth and flowers of this new variety in different stages of development, depicted in color as nearly true as it is reasonably possible to make the same in a color illustration of this character.

DETAILED BOTANICAL DESCRIPTION

The following is a detailed description of my new rose cultivar with color descriptions using terminology in accordance with The Royal Horticultural Society (London) Colour Chart© 2001, except where ordinary dictionary significance of color is indicated.

Parentage:
*Seed Parent.*—Unnamed seedling (not patented). Parentage of the unnamed seed parent is Unnamed seedling×unnamed seedling.
*Pollen Parent.*—'JACshok' (PP 11,562).

FLOWER

Observations made from January 2006 to June 2007 from plants commencing at two to three years of age grown in a garden environment at Somis, Calif.

Blooming habit: Continuous.

Bud:

*Size.*—About 25 mm long and 20 mm in diameter when the petals start to unfurl.

*Form.*—The bud form is long, blunt topped.

*Color.*—When sepals first divide, bud color is Red-Purple Group 60A. When half blown, the upper sides of the petals are between Red-Purple Group 60C and the lower sides of the petals are Greyed-Purple Group 186D except on petal edges where they are Greyed-Purple Group 186B.

*Sepals.*—Color: Upper surface: Green Group 138B. Lower surface: Yellow-Green Group 137D, often with Greyed-Purple Group 183C. Length: 20 mm. Width: 7 mm. Shape: Subulate. Surface texture: Hoary. There are three lightly appendaged sepals. There are two unappendaged sepals with hairy edges.

*Receptacle.*—Color: Green Group 137D. Shape: Funnel. Size: Medium, about 6 mm long×6 mm wide.

*Peduncle.*—Surface: Smooth with a few glands. Color: Green Group 137D, often overlain with Greyed Purple Group 186D. Strength: Stiff.

Bloom:

*Size.*—Medium. Average open diameter is about 80–90 mm.

*Borne.*—Several together in clusters of 3–9 blooms having rounded shape.

*Stems.*—Strength: Strong. Average length is about 30–40 cm with a diameter of 6–7 mm.

*Form.*—When first open: Cupped. Permanence: Retains its form to the end.

*Petalage.*—Number of petals under normal conditions: 10–15. Color: The upper sides of the petals are Red-Purple Group 60C. The reverse sides of the petals are Greyed-Purple Group 186D except on petal edges which are Greyed-Purple Group 186B. The base of the petals has a distinct approximately 5 mm×5 mm Yellow Group 8D color spot. The major color on the upper sides is Red-Purple Group 60C.

*Variegations.*—None observed.

*Discoloration.*—The general tonality at the end of the first day: No change. At the end of the third day: No change. Further aging: By day 4 or 5 the petals fade to Greyed-Purple Group 186D.

*Fragrance.*—Strong. Lemon.

Petals:

*Texture.*—Thick.

*Surface.*—Smooth.

*Shape.*—Orbicular.

*Margin.*—Entire.

*Apex Shape.*—Obtuse.

*Base Shape.*—Rounded.

*Form.*—Flat.

*Arrangement.*—Imbricated.

*Petaloids.*—Number: None to up to 3, 1–3 mm long×3–9 mm wide. Color: The upper sides of the petaloids are Red-Purple Group 60C. The lower sides of the petaloids are Greyed-Purple Group 186D.

*Persistence.*—Petals drop off cleanly before drying.

*Lastingness.*—On the plant: Fair (about 5 days). As a cut flower: Fair (about 5 days).

Reproductive Parts:

*Stamens.*—Number: 40–50. Length: 6–12 mm. Anthers: Length: 1–2 mm. Color: Yellow-Orange Group 17B. Arrangement: Regular around styles. Filaments: Color: Yellow Group 13D. Length: 4–11 mm Pollen: Color: Greyed-Orange Group 168C.

*Pistils.*—Number: 20–30. Length: 5–7 mm. Styles: Color: Green-Yellow Group 1D. Length: 4–6 mm. Stigmas: Color: Greyed-Orange Group 163B. Length: 1 mm.

*Hips.*—None observed.

PLANT

*Form.*—Bush, shrub.

*Growth.*—Vigorous, upright, branching.

*Age at maturity.*—Two years.

*Mature plant.*—Height: 4 ft. Width: 3 ft.

*Rootstock.*—Own root.

Foliage: Number of leaflets on normal mid-stem leaves: 5–7.

*Size.*—Large. About 14–18 cm long×12–14 cm wide.

*Quantity.*—Normal.

*Color.*—New foliage: Upper side: Yellow-Green Group 146C with Greyed-Red Group 178A. Lower side: Yellow-Green Group 146D with Greyed-Orange Group 176C. Old foliage: Upper side: Yellow-Green Group 147A. Lower side: Green Group 137A.

Leaflets:

*Size.*—About 5–8 cm long×2.5–4 cm wide.

*Shape.*—Pointed oval.

*Base shape.*—Oblique.

*Apex Shape.*—Acuminate.

*Texture.*—Leathery.

*Edge.*—Serrated.

*Serrations.*—Double, small.

*Petiole.*—Color: Upper: Yellow-Green Group 147A. Lower: Yellow-Green Group 144B.

*Petiole rachis.*—Color: Yellow-Green Group 144B. Underside: Occasional prickles.

*Auricles.*—Subulate.

*Stipules.*—Length: 25–30 mm, bearded.

*Disease resistance.*—Resistant to mildew and rust, susceptible to blackspot under normal growing conditions.

*Pest resistance.*—None observed.

*Vein color.*—Yellow-Green Group 147B.

*Venation pattern.*—Reticulate.

Wood:

*New wood.*—Color: Greyed-Red Group 178B. Bark: Smooth.

*Old wood.*—Color: Green Group 137D. Bark: Smooth.

Prickles:

*Quantity.*—On main canes from base: Ordinary, 15 per 150 mm of cane. On laterals from main canes: Ordinary, 15 per 150 mm of cane.

*Form.*—Hooked slightly upward.

*Length.*—5 mm.

*Color when young.*—Greyed-Red Group 178B.

*Color when mature.*—Greyed-Orange Group 166A.

I claim:

1. A new and distinct variety of rose plant of the shrub class, substantially as herein shown and described, characterized particularly by its dark purple flower color; strong lemon fragrance; vigorous, upright growth; large clusters, ease of rooting as a softwood or hardwood cutting; and excellent resistance to rust and powdery mildew.

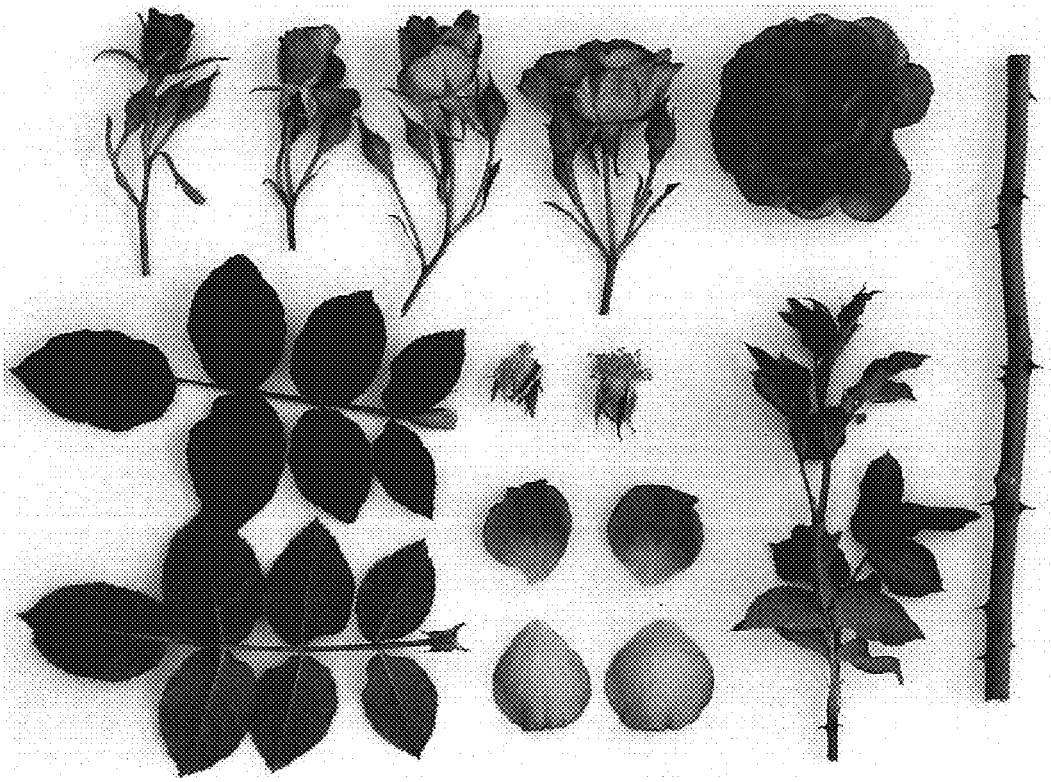

* * * * *